United States Patent
Han et al.

(10) Patent No.: US 12,357,666 B1
(45) Date of Patent: Jul. 15, 2025

(54) TRADITIONAL CHINESE HERBAL PLANT COMPOSITION FOR IMPROVING SYMPTOMS OF LIVER CANCER PATIENTS AND COMPATIBILITY METHOD THEREOF

(71) Applicant: The First Hospital of China Medical University, Shenyang (CN)

(72) Inventors: Tao Han, Shenyang (CN); Jing Li, Shenyang (CN); Tingsong Chen, Shenyang (CN)

(73) Assignee: The First Hospital of China Medical University, Shenyang (CN)

( * ) Notice: Subject to any disclaimer, the term of this patent is extended or adjusted under 35 U.S.C. 154(b) by 0 days.

(21) Appl. No.: 19/077,428

(22) Filed: Mar. 12, 2025

(30) Foreign Application Priority Data

Aug. 2, 2024 (CN) .......................... 202411057568.7

(51) Int. Cl.
| | |
|---|---|
| *A61K 36/67* | (2006.01) |
| *A61K 36/481* | (2006.01) |
| *A61K 36/484* | (2006.01) |
| *A61K 36/60* | (2006.01) |
| *A61K 36/704* | (2006.01) |
| *A61K 36/898* | (2006.01) |
| *A61P 35/00* | (2006.01) |

(52) U.S. Cl.
CPC ............ *A61K 36/67* (2013.01); *A61K 36/481* (2013.01); *A61K 36/484* (2013.01); *A61K 36/60* (2013.01); *A61K 36/704* (2013.01); *A61K 36/898* (2013.01); *A61P 35/00* (2018.01); *A61K 2236/331* (2013.01)

(58) Field of Classification Search
None
See application file for complete search history.

(56) References Cited

U.S. PATENT DOCUMENTS

2004/0175439 A1* 9/2004 Cyr ...................... A61K 8/9761
435/7.1

* cited by examiner

*Primary Examiner* — H. Sarah Park
(74) *Attorney, Agent, or Firm* — Westbridge IP LLC

(57) ABSTRACT

Disclosed are a traditional Chinese herbal plant composition for improving symptoms of liver cancer patients and a compatibility method thereof. The herbal plant composition consists of the following raw materials by weight: 20-28 parts of yangtao *actinidia* root (*Actinidia chinensis* Planch.), 17-22 parts of bird's-foot trefoil (*Lotus corniculatus* L.), 12-15 parts of shorthairy antenoron (*Anoectochilus roxburghii* (Wall.) Lindl.), 7-10 parts of giant knotweed rhizome (*Polygoni Cuspidati Rhizoma* et *Radix*), 1-5 parts of fruit of mountain spicy tree (*Piper cubeba* L.f.), 5-10 parts of *astragalus* milkvetch root (*Astragali Radix*), 1-5 parts of hispid fig root (*Ficus simplicissima* Lour.), and 1-3 parts of liquorice root (*Glycyrrhizae Radix* et *Rhizoma*). The herbal plant composition can inhibit the growth of liver cancer cells without side effects.

8 Claims, No Drawings

TRADITIONAL CHINESE HERBAL PLANT COMPOSITION FOR IMPROVING SYMPTOMS OF LIVER CANCER PATIENTS AND COMPATIBILITY METHOD THEREOF

CROSS-REFERENCE TO RELATED APPLICATIONS

This application claims priority to Chinese Patent Application No. 202411057568.7, filed on Aug. 2, 2024, the content of which is incorporated herein by reference in its entirety.

TECHNICAL FIELD

The present application belongs to the technical field of medicine, and in particular relates to a traditional Chinese herbal plant composition for improving symptoms of liver cancer patients and a compatibility method thereof.

BACKGROUND

Malignant tumors have the characteristics of high mortality, short survival time, poor quality of life, etc. Liver cancer, also known as liver malignancy, is the sixth most common cancer and the fourth leading cause of cancer death, posing a serious threat to human health. At present, treatment means for liver cancer include resection, chemoradiotherapy, intervention, targeted drugs, immunotherapy, traditional Chinese medicine, etc., among which resection is the main treatment means. However, due to high occult and rapid progression of liver cancer in the early stage, most liver cancer patients are already in the middle to advanced stages when diagnosed. Moreover, liver cancer cell lesions tend to be multiple and easy to spread, so less than 30% of liver cancer patients are eligible for liver cancer resection. Clinical studies have found that surgical resection is often accompanied by many complications, and there is also the problem of poor prognosis.

Research has found that combined therapy based on traditional Chinese medicine is of great significance in controlling the progression of liver cancer patients, improving their quality of life, and prolonging their survival time. Moreover, Chinese herbal formulas have high efficacy and safety in clinical treatment and prevention of tumors, and therefore have attracted much attention in the field of medicine. At present, the anti-liver cancer effect of existing Chinese formulas is unclear, so there is a high demand in this field for new drugs capable of effectively treating liver cancer, in order to achieve effective treatment of liver cancer. Therefore, there is an urgent need to provide a herbal plant composition for treating liver cancer with more stable and significant therapeutic effects.

SUMMARY

A first object of the present application is to provide a traditional Chinese herbal plant composition for improving symptoms of liver cancer patients, which can inhibit the growth of liver cancer cells without side effects.

A second object of the present application to provide a compatibility method for a traditional Chinese herbal plant composition for improving symptoms of liver cancer patients, which is simple in steps and easy to operate.

In order to achieve the above objects, the present application uses the following technical solutions.

A traditional Chinese herbal plant composition for improving symptoms of liver cancer patients consists of the following raw materials by weight: 20-28 parts of yangtao *actinidia* root (*Actinidia chinensis* Planch.), 17-22 parts of bird's-foot trefoil (*Lotus corniculatus* L.), 12-15 parts of shorthairy *antenoron* (*Anoectochilus roxburghii* (Wall.) Lindl.), 7-10 parts of giant knotweed rhizome (*Polygoni Cuspidati Rhizoma* et *Radix*), 1-5 parts of fruit of mountain spicy tree (*Piper cubeba* L.f.), 5-10 parts of *astragalus* milkvetch root (*Astragali Radix*), 1-5 parts of hispid fig root (*Ficus simplicissima* Lour.), and 1-3 parts of liquorice root (*Glycyrrhizae Radix* et *Rhizoma*).

Further, the herbal plant composition consists of the following raw materials by weight: 25 parts of yangtao *actinidia* root, 19 parts of bird's-foot trefoil, 13 parts of shorthairy *antenoron,* 8 parts of giant knotweed rhizome, 3 parts of fruit of mountain spicy tree, 7 parts of *astragalus* milkvetch root, 4 parts of hispid fig root, and 2 parts of liquorice root.

Further, the yangtao *actinidia* root is root of *Actinidia chinensis.*

A compatibility method of the herbal plant composition described above includes the following steps: (1) weighing the crude drugs according to the parts by weight described above and mixing evenly, adding water for soaking, decocting, and then filtering to obtain a first filtrate; (2) adding water to dregs obtained by filtering a first decoction liquid in step (1) for soaking, decocting, and then filtering to obtain a second filtrate; and (3) combining the first filtrate and the second filtrate and concentrating to an extract having a relative density of 1.0 to 1.1.

Further, the amount of water used in the steps (1) and (2) is 20-30 times the total weight of the crude drugs.

Further, in the step (1), the soaking time is 2-3 h, and the decocting time is 3-4 h; and in the step (2), the soaking time is 3-4 h, and the decocting time is 3-4 h.

Further, excipients are added to the herbal plant composition to prepare a corresponding dosage form.

Further, the dosage form is an oral dosage form.

Further, the oral dosage form is oral liquid, tablet, powder, granule or capsule.

Pharmacological properties of the crude drugs used in the present application are analyzed as follows.

Root of *Actinidia chinensis*: [Nature and flavor and channel tropism] Sweet and astringent in taste, cool in nature. Enter heart, kidney, liver and spleen channels. [Functions and indications] Clearing heat and removing toxicity, dispelling pathogenic wind and promoting diuresis, promoting blood circulation and reducing swelling; indicated for hepatitis, dyspepsia, edema, sore and furuncle, scrofuloderma, gastrointestinal tumor, breast cancer, etc.

Bird's-foot trefoil: [Nature and flavor and channel tropism] Sweet and bitter in taste, slightly cold in nature. Enter the lung channel. [Functions and indications] Tonifying deficiency, clearing heat, and quenching thirst; indicated for consumptive disease, acratia, fever due to yin deficiency, dry throat, thirst, etc. The *Tang materia medica of China* records "keeping the adverse qi downward, quenching thirst, dispelling heat, eliminating consumptive disease and fatigue, and tonifying deficiencies."

Shorthairy *antenoron*: [Nature and flavor and channel tropism] Sweet in taste, neutral in nature. Enter lung, liver, kidney and urinary bladder channels. [Functions and indications] Clearing heat and cooling blood, dispelling wind and eliminating dampness, and removing toxicity. Indicated for sore and ulcer, toxic swelling, tumors, etc.

Giant knotweed rhizome: [Nature and flavor and channel tropism] Slightly bitter in taste, slightly cold in nature. Enter liver, gallbladder and lung channels. [Functions and indications] Promoting diuresis and removing jaundice, clearing heat and removing toxicity, dissipating blood stasis and relieving pain, and expelling phlegm and relieving cough. Indicated for gallstones, liver dysfunction, fatty liver, pain, etc.

Fruit of mountain spicy tree: [Nature and flavor and channel tropism] Acrid in taste, warm in nature. Enter spleen, stomach, kidney and urinary bladder channels. [Functions and indications] Warming spleen and stomach for dispelling cold, promoting the circulation of qi and relieving pain, and promoting the function of gallbladder. Indicated for gastrofrigid vomiting, abdominal cold pain, diarrhea, cholecystitis, gallstones, etc.

*Astragalus* milkvetch root: [Nature and flavor and channel tropism] Sweet in taste, warm in nature. Enter lung and spleen channels. [Functions and indications] Benefiting qi and invigorating vital function, consolidating superficies for arresting sweating, inducing diuresis for removing edema, expelling toxin to drain pus, and promoting wound healing and promoting granulation. Indicated for diarrhea due to hypofunction of the spleen, spontaneous sweating, edema, and other symptoms of qi deficiency and blood deficiency.

Hispid fig root: [Nature and flavor and channel tropism] Sweet in taste, neutral in nature. Enter spleen, lung and liver channels. [Functions and indications] Strengthening the spleen and tonifying the lung, promoting the circulation of qi and promoting diuresis, and relieving rigidity of muscles and activating collaterals. Indicated for spleen asthenic dropsy, asthenia due to eating less, pulmonary tuberculosis, cough, night sweating, leukorrhea, postpartum agalactia, menstrual disorders, rheumatic arthralgia, edema, etc.

Liquorice root: [Nature and flavor and channel tropism] Sweet in taste, neutral in nature. Enter spleen, stomach, heart and lung channels. [Functions and indications] Regulating the middle and relaxing spasm, moistening the lung, clearing heat and removing toxicity, and harmonizing various medicines. Indicated for shortness of breath, acratia, loose stool due to eating less, cough and gasp, swelling and pain in throat, etc. The *Variorum of Shennong's Classic of Materia Medica* records that it is indicated for cold and heat, and pathogenic qi in the five viscera and six bowels, strengthening sinews and bones, promoting the growth of muscle, enhancing physical strength, incised wounds and swelling, and removing toxicity.

Compared with the prior art, the beneficial effects of the present application are as follows.

The present application provides a traditional Chinese herbal plant composition for improving symptoms of liver cancer patients. In the formula, the yangtao *actinidia* root clears heat and removes toxicity, promotes blood circulation and relieves pain, the bird's-foot trefoil tonifies deficiency and clears heat, and the two crude drugs are combined as a sovereign drug to strengthen vital qi to eliminate pathogenic factor; the shorthairy *antenoron* dispels pathogenic wind and removes toxicity, clear heat and cool blood, the giant knotweed rhizome dissipates blood stasis and relieves pain, clears heat and removes toxicity, and the two crude drugs are combined as a minister drug to clear heat, nourish yin, and remove blood stasis; the fruit of mountain spicy tree promotes the circulation of qi and relieves pain, the *astragalus* milkvetch root invigorates qi and invigorate vital function, the hispid fig root relieves rigidity of muscles and activates collaterals, and the three crude drugs are combined as an assistant drug to invigorate qi and warm yang; and the liquorice root harmonizes the drugs and ushers the drugs to affected channels to jointly play a role in removing blood stasis, softening hard masses, strengthening vital qi to eliminate pathogenic factor, and warming the spleen and dredging channels. The combination of the above crude drugs can inhibit the growth of liver cancer cells without side effects, providing a new idea for the treatment of liver cancer.

DETAILED DESCRIPTION OF THE EMBODIMENTS

The technical solutions of the present application will be further described below in conjunction with specific embodiments. However, it will be understood by those skilled in the art that the following embodiments are merely for illustration of the present application and should not be considered as limitation to the present application. Specific conditions not specified in the embodiments followed conventional conditions or conditions recommended by the manufacturer. The reagents or instruments used, unless otherwise specified, were commercially available conventional products.

EMBODIMENTS

Embodiment 1

The present embodiment provides a traditional Chinese herbal plant composition for improving symptoms of liver cancer patients, where the herbal plant composition consisted of the following raw materials by weight: 25 parts of root of *Actinidia chinensis*, 19 parts of bird's-foot trefoil, 13 parts of shorthairy *antenoron*, 8 parts of giant knotweed rhizome, 3 parts of fruit of mountain spicy tree, 7 parts of *astragalus* milkvetch root, 4 parts of hispid fig root, and 2 parts of liquorice root.

The present embodiment also provides a compatibility method of the herbal plant composition, and a specific preparation process is as follows: (1) the crude drugs were weighed according to the above-mentioned parts by weight and mixed evenly, and then placed into a high-necked round bottom flask; distilled water was added to the high-necked round bottom flask at a ratio of the amount of distilled water added to the total weight of the crude drugs being 25:1 to soak the crude drugs for 2.5 h, and then the crude drugs were decocted for 3.2 h; and a first decoction liquid resulting from the decoction was filtered with 2 layers of gauze, 4 layers of gauze, 8 layers of gauze and 16 layers of gauze successively, resulting in a first filtrate; (2) dregs obtained by filtering the first decoction liquid in step (1) were placed into a high-necked round bottom flask, the same amount of distilled water as that in the step (1) was added to the high-necked round bottom flask to soak for 3.5 h, then the dregs were decocted for 3.5 h; and a second decoction liquid resulting from the decoction was filtered with 3 layers of gauze, 6 layers of gauze, 12 layers of gauze and 20 layers of gauze successively, resulting in a second filtrate; and (3) the first filtrate and the second filtrate were combined and concentrated to an extract having a relative density of 1.03.

Embodiment 2

The present embodiment provides a traditional Chinese herbal plant composition for improving symptoms of liver cancer patients, where the herbal plant composition consisted of the following raw materials by weight: 20 parts of root of *Actinidia chinensis*, 17 parts of bird's-foot trefoil, 12 parts of shorthairy *antenoron*, 7 parts of giant knotweed rhizome, 1 part of fruit of mountain spicy tree, 5 parts of *astragalus* milkvetch root, 1 part of hispid fig root, and 1 part of liquorice root.

The present embodiment also provides a compatibility method of the herbal plant composition, and a specific preparation process is as follows: (1) the crude drugs were weighed according to the above-mentioned parts by weight and mixed evenly, and then placed into a high-necked round bottom flask; distilled water was added to the high-necked round bottom flask at a ratio of the amount of distilled water added to the total weight of the crude drugs being 20:1 to soak the crude drugs for 3 h, and then the crude drugs were decocted for 4 h; and a first decoction liquid resulting from the decoction was filtered with 2 layers of gauze, 4 layers of gauze, 8 layers of gauze and 16 layers of gauze successively, resulting in a first filtrate; (2) dregs obtained by filtering the first decoction liquid in step (1) were placed into a high-necked round bottom flask, the same amount of distilled water as that in the step (1) was added to the high-necked round bottom flask to soak for 3 h, then the dregs were decocted for 4 h; and a second decoction liquid resulting from the decoction was filtered with 3 layers of gauze, 6 layers of gauze, 12 layers of gauze and 20 layers of gauze successively, resulting in a second filtrate; and (3) the first filtrate and the second filtrate were combined and concentrated to an extract having a relative density of 1.1.

Embodiment 3

The present embodiment provides a traditional Chinese herbal plant composition for improving symptoms of liver cancer patients, where the herbal plant composition consisted of the following raw materials by weight: 28 parts of root of *Actinidia chinensis*, 22 parts of bird's-foot trefoil, 15 parts of shorthairy *antenoron*, 10 parts of giant knotweed rhizome, 5 parts of fruit of mountain spicy tree, 10 parts of *astragalus* milkvetch root, 5 parts of hispid fig root, and 3 parts of liquorice root.

The present embodiment also provides a compatibility method of the herbal plant composition, and a specific preparation process is as follows: (1) the crude drugs were weighed according to the above-mentioned parts by weight and mixed evenly, and then placed into a high-necked round bottom flask; distilled water was added to the high-necked round bottom flask at a ratio of the amount of distilled water added to the total weight of the crude drugs being 30:1 to soak the crude drugs for 2 h, and then the crude drugs were decocted for 3 h; and a first decoction liquid resulting from the decoction was filtered with 2 layers of gauze, 4 layers of gauze, 8 layers of gauze and 16 layers of gauze successively, resulting in a first filtrate; (2) dregs obtained by filtering the first decoction liquid in step (1) were placed into a high-necked round bottom flask, the same amount of distilled water as that in the step (1) was added to the high-necked round bottom flask to soak for 4 h, then the dregs were decocted for 3 h; and a second decoction liquid resulting from the decoction was filtered with 3 layers of gauze, 6 layers of gauze, 12 layers of gauze and 20 layers of gauze successively, resulting in a second filtrate; and (3) the first filtrate and the second filtrate were combined and concentrated to an extract having a relative density of 1.0.

COMPARATIVE EXAMPLES

Comparative Example 1

The comparative example provides a herbal plant composition, where the herbal plant composition consisted of the following raw materials by weight: 25 parts of root of *Actinidia chinensis*, 13 parts of shorthairy *antenoron*, 8 parts of giant knotweed rhizome, 3 parts of fruit of mountain spicy tree, 7 parts of *astragalus* milkvetch root, 4 parts of hispid fig root and 2 parts of liquorice root, with the rest the same as in Embodiment 1.

Comparative Example 2

The comparative example provides a herbal plant composition, where the herbal plant composition consisted of the following raw materials by weight: 25 parts of root of *Actinidia chinensis*, 19 parts of bird's-foot trefoil, 21 parts of giant knotweed rhizome, 3 parts of fruit of mountain spicy tree, 7 parts of *astragalus* milkvetch root, 4 parts of hispid fig root and 2 parts of liquorice root, with the rest the same as in Embodiment 1.

Comparative Example 3

The comparative example provides a herbal plant composition, where the herbal plant composition consisted of the following raw materials by weight: 25 parts of root of *Actinidia chinensis*, 19 parts of bird's-foot trefoil, 21 parts of shorthairy *antenoron*, 3 parts of fruit of mountain spicy tree, 7 parts of *astragalus* milkvetch root, 4 parts of hispid fig root and 2 parts of liquorice root, with the rest the same as in Embodiment 1.

EFFECT EXAMPLES

Effect Example 1

The effect example explored the inhibitory effects of the herbal plant compositions of Embodiments 1-3 and Comparative Examples 1-3 on Hep G2 tumor cells, and a specific process is as follows.

The extracts of Embodiments 1-3 and Comparative Examples 1-3 were diluted to concentrations of 10 mg/mL, 40 mg/mL and 80 mg/mL using RPMI-1640 complete medium, and filtered and sterilized using 0.25 μm sterile syringe filters to obtain drug-containing media for later use. In addition to the drug-containing medium group, a negative control group without the drugs and a pure culture medium group were set, and 5 replicate wells were set for all groups.

The Hep G2 cells were resuspended in the RPMI-1640 complete medium, and a cell density was adjusted to $5\times10^4$ cells/mL, resulting in a Hep G2 cell suspension. The Hep G2 cell suspension was added to a 96-well plate, with 100 μL per well, and cultured in a 37° C. and 5% $CO_2$ cell incubator for 24 h. After the cells adhered to the wall, a resulting supernatant was discarded, 100 μL of each group of drug-containing medium was added to each well to incubate the cells in the 37° C. and 5% $CO_2$ cell incubator for 72 h. After the incubation, 10 μL of CCK-8 solution was added to each well to continuously culture the cells in the incubator for 4 h. Then, an OD value of each group of cells at 450 nm was detected using a microplate reader, the inhibition rate was calculated as (OD value of negative control group-OD value of administration group)/(OD value of negative control group-OD value of pure medium group)×100%, and the OD value of each group was an average of the 5 replicate wells. The results are shown in Table 1.

TABLE 1

| Group/inhibition rate | 10 mg/mL | 40 mg/mL | 80 mg/mL |
|---|---|---|---|
| Embodiment 1 | 3.05% | 27.60% | 96.24% |
| Embodiment 2 | 2.94% | 27.15% | 95.83% |
| Embodiment 3 | 2.86% | 26.33% | 95.17% |
| Comparative Example 1 | 1.81% | 17.48% | 83.69% |
| Comparative Example 2 | 2.53% | 24.09% | 92.86% |
| Comparative Example 3 | 2.12% | 22.85% | 91.15% |

It can be seen from Table 1 that when the drug concentration was 10-80 mg/mL, the herbal plant compositions of Embodiments 1-3 can inhibit the growth of liver cancer cells to varying degrees after 72 h of administration, and the drug concentration of 80 mg/mL resulted in the best inhibitory effect.

Compared with Embodiments 1-3, the inhibition rate of Hep G2 cells in Comparative Example 1 group was significantly reduced, and the inhibition rate of Hep G2 cells in Comparative Example 2-3 group was slightly reduced. It can be seen therefrom that the herbal plant composition formula of the present application can inhibit the growth of liver cancer cells.

Effect Example 2

The effect example explored the anti-tumor effect of the herbal plant compositions of Embodiment 1 and Comparative Examples 1 to 3 on tumor mice, and a specific process is as follows.

I. Test Materials

Totally 90 male BALB/c nude mice aged 5 weeks and with body weight of 19-22 g were used.

II. Construction of Tumor Cell Model

A total of 80 BALB/c nude mice were randomly selected and injected subcutaneously with Hep G2 cell line ($5 \times 10^6$ cells) in the right armpits. After 10 d, a mass appeared in the right armpits of the nude mice, indicating that the tumor cell model was successfully established.

III. Grouping and Dosing

Dosing Criteria: the conventional gavage dose of mice was 103.5 g/kg×0.0026×50=10.53 g/kg. Generally, it is also necessary to increase the dose of the original medicinal material of the herbal plant composition by 1 time and decrease the dose of the original medicinal material of the herbal plant composition by 1 time for gavage.

Model group: 10 mice, administered equal volume of physiological saline by gavage.

Low-dose Embodiment 1 Herbal Plant Composition Group: 10 mice, administered 5.27 g/kg Embodiment 1 herbal plant composition by gavage.

Medium-dose Embodiment 1 Herbal Plant Composition Group: 10 mice, administered 10.53 g/kg Embodiment 1 herbal plant composition by gavage.

High-dose Embodiment 1 Herbal Plant Composition Group: 10 mice, administered 21.06 g/kg Embodiment 1 herbal plant composition by gavage.

High-dose Comparative Example 1 Herbal Plant Composition Group: 10 mice, administered 21.06 g/kg Comparative Example 1 herbal plant composition by gavage.

High-dose Comparative Example 2 Herbal Plant Composition Group: 10 mice, administered 21.06 g/kg Comparative Example 2 herbal plant composition by gavage.

High-dose Comparative Example 3 Herbal Plant Composition Group: 10 mice, administered 21.06 g/kg Comparative Example 3 herbal plant composition by gavage.

Western medicine control group: 10 mice, administered 0.03 g/kg 5-fluorouracil by gavage.

Blank control group: 10 mice, administered equal volume of physiological saline by gavage.

IV. Detection of Tumor Inhibition Rate of Each Group

After 28 d of continuous administration, the mice in each group were weighed and killed by cervical dissection. Tumors and organs (lung, liver, heart and kidney) of the mice in each group were removed under sterile conditions, and washed with physiological saline. After washing, the tumors and the organs were dried with filter paper, weighed to obtain mass and recorded, and the tumor inhibition rate and organ index were calculated. The tumor mass of the mice was the average value of the tumor mass of each group of mice. Tumor inhibition rate=(tumor mass of mice in the model group-tumor mass of mice in the test group)/tumor mass of mice in the model group×100%. The tumor mass and tumor inhibition rate of mice in each group are shown in Table 2. Organ index (mg/g)=organ mass (mg)/body mass (g) of mice. The organ index is the average value of the organ index of each group of mice, and the results are shown in Table 3.

TABLE 2

| Grouping | Dosage | Tumor mass (g) | Inhibition rate (%) |
|---|---|---|---|
| Model group | / | 0.52 | / |
| Western medicine control group | 0.03 g/kg | 0.27 | 48.07 |
| Low-dose Embodiment 1 | 5.27 g/kg | 0.44 | 15.38 |
| Medium-dose Embodiment 1 | 10.53 g/kg | 0.30 | 42.31 |
| High-dose Embodiment 1 | 21.06 g/kg | 0.28 | 46.15 |
| High-dose Comparative Example 1 | 21.06 g/kg | 0.42 | 19.23 |
| High-dose Comparative Example 2 | 21.06 g/kg | 0.35 | 32.69 |
| High-dose Comparative Example 3 | 21.06 g/kg | 0.37 | 28.85 |

TABLE 3

| Grouping | Dosage | Liver index (mg/g) | Renal index (mg/g) | Lung index (mg/g) | Cardiac Index (mg/g) |
|---|---|---|---|---|---|
| Model group | / | 42.31 | 17.25 | 5.62 | 4.87 |
| Western medicine control group | 0.03 g/kg | 42.78 | 17.69 | 5.96 | 5.13 |
| Low-dose Embodiment 1 | 5.27 g/kg | 42.64 | 17.52 | 5.87 | 5.05 |
| Medium-dose Embodiment 1 | 10.53 g/kg | 42.91 | 17.60 | 6.24 | 5.17 |
| High-dose Embodiment 1 | 21.06 g/kg | 42.38 | 17.41 | 5.69 | 4.92 |
| High-dose Comparative Example 1 | 21.06 g/kg | 42.80 | 17.72 | 5.83 | 5.10 |
| High-dose Comparative Example 2 | 21.06 g/kg | 42.47 | 17.50 | 5.72 | 4.95 |
| High-dose Comparative Example 3 | 21.06 g/kg | 42.51 | 17.48 | 5.75 | 4.99 |

As can be seen from Table 2, the medium-dose herbal plant composition, the high-dose herbal plant composition and the western medicine group had relatively high tumor inhibition rates in mice, indicating that the medium-dose and high-dose herbal plant compositions can be applied to the treatment of liver cancer.

As can be seen from Table 3, compared to the model group, the liver index, renal index, lung index and cardiac index of the tumor mice in the model group, the low-dose herbal plant composition group, the medium-dose herbal plant composition group, the high-dose herbal plant composition group and the western medicine control group showed no significant change. The above results indicate that the herbal plant composition of the present application has no effect on the major organ index of tumor mice. That is, the herbal plant composition of the present application can effectively treat liver cancer without side effects.

Finally, it is to be understood that the above embodiments are merely illustrative of the technical solutions of the present application, and are not restrictive to them. The basic principles and main features of the present application have been described above with specific embodiments, and some modifications or substitutions may be made on the basis of the present application, but these modifications or substitutions do not make the essence of the corresponding technical solution deviate from the claimed scope of the present application.

What is claimed is:

1. A traditional Chinese herbal plant composition for ameliorating symptoms of liver cancer in patients, wherein the herbal plant composition consists of the following raw materials by weight: 20-28 parts of yangtao *actinidia* root (*Actinidia chinensis* Planch.), 17-22 parts of bird's-foot trefoil (*Lotus corniculatus* L.), 12-15 parts of shorthairy antenoron (*Anoectochilus roxburghii* (Wall.) Lindl.), 7-10 parts of giant knotweed rhizome (*Polygoni Cuspidati Rhizoma* et *Radix*), 1-5 parts of fruit of mountain spicy tree (*Piper cubeba* L.f.), 5-10 parts of *astragalus* milkvetch root (*Astragali Radix*), 1-5 parts of hispid fig root (*Ficus simplicissima* Lour.), and 1-3 parts of liquorice root (*Glycyrrhizae Radix* et *Rhizoma*).

2. The herbal plant composition according to claim 1, wherein the herbal plant composition consists of the following raw materials by weight: 25 parts of the yangtao *actinidia* root, 19 parts of the bird's-foot trefoil, 13 parts of the shorthairy *antenoron,* 8 parts of the giant knotweed rhizome, 3 parts of the fruit of mountain spicy tree, 7 parts of the *astragalus* milkvetch root, 4 parts of the hispid fig root, and 2 parts of the liquorice root.

3. A preparation method of the herbal plant composition according to claim 1, comprising the following steps:
   (1) weighing the crude drugs according to the parts by weight and mixing evenly, adding water for soaking, decocting, and then filtering to obtain a first filtrate, and retaining dregs;
   (2) adding water to the dregs of step (1) for soaking, decocting, and then filtering to obtain a second filtrate; and
   (3) combining the first filtrate and the second filtrate and concentrating to an extract having a relative density of 1.0 to 1.1.

4. The preparation method of the herbal plant composition according to claim 3, wherein the amount of water used in the step (1) and the step (2) is 20-30 times the total weight of the crude drugs.

5. The preparation method of the herbal plant composition according to claim 3, wherein in the step (1), the soaking time is 2-3 h, and the decocting time is 3-4 h; and in the step (2), the soaking time is 3-4 h, and the decocting time is 3-4 h.

6. The preparation method of the herbal plant composition according to claim 3, wherein excipients are added to the herbal plant composition to prepare a dosage form.

7. The preparation method of the herbal plant composition according to claim 6, wherein the dosage form is an oral dosage form.

8. The preparation method of the herbal plant composition according to claim 7, wherein the oral dosage form is oral liquid, tablet, powder, granule or capsule.

* * * * *